US012121548B1

(12) United States Patent
Elsherif et al.

(10) Patent No.: US 12,121,548 B1
(45) Date of Patent: Oct. 22, 2024

(54) METHOD FOR SYNTHESIZING A SILVER NANOPARTICLE COMPOSITION FROM RHYNCHOPHORUS FERRUGINEUS LARVAE OLIVIER

(71) Applicant: KING FAISAL UNIVERSITY, Al-Ahsa (SA)

(72) Inventors: Fadia Elsherif, Al-Ahsa (SA); Salaheldin Hassan Khattab, Al-Ahsa (SA); Munirah Fahad Aldayel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 39 days.

(21) Appl. No.: 18/203,772

(22) Filed: May 31, 2023

(51) Int. Cl.
*A61K 35/64* (2015.01)
*A61K 9/51* (2006.01)
*A61K 33/38* (2006.01)
*A61P 31/04* (2006.01)

(52) U.S. Cl.
CPC ............ *A61K 35/64* (2013.01); *A61K 9/5192* (2013.01); *A61K 33/38* (2013.01); *A61P 31/04* (2018.01)

(58) Field of Classification Search
None
See application file for complete search history.

(56) References Cited

PUBLICATIONS

Abdel-Raheem et al, 2019. Egyptian Journal of Biological Pest Control, 29:97, pp. 1-5 (Year: 2019).*

Iravani et al., Synthesis of silver nanoparticles: chemical, physical and biological methods, 2014, Research in Pharmaceutical Sciences, 9(6): 385-406.*

University of Florence, Italy; Università degli Studi di Palermo, "Antimicrobial activity of the Red Palm Weevil Rhynchophorus ferrugineus".

King Abdulaziz University Saudi Arabia; "Gut Extracts of Rhynchophorus ferrugineus Larvae Olivier Affecting Bacterial Dental Caries".

Jagiellonian University, Poland Cairo University; AGH University of Science and Technology, "Isolation, Identification, and Bioinformatic Analysis of Antibacterial Proteins and Peptides from Immunized Hemolymph of Red Palm Weevil Rhynchophorus ferrugineus".

King Abdulaziz University; Cairo University, "In Vitro Evaluation of Antimicrobial Activity of Alimentary Canal Extracts from the Red Palm Weevil, Rhynchophorus ferrugineus Olivier Larvae".

King Faisal University, Al-Ahsa, Saudi Arabia, "Detection of Insect Immunity Substances (Lectins) in the Midgut Extracts from Larvae and Adult Red Palm Weevil Rhynchophorus ferrugineus (Olivier) in Al-Ahsa, Saudi Arabia".

* cited by examiner

*Primary Examiner* — Terry A McKelvey
*Assistant Examiner* — Catheryne Chen
(74) *Attorney, Agent, or Firm* — Nath, Goldberg & Meyer; Joshua B. Goldberg

(57) ABSTRACT

*Rhynchophorus ferrugineus* silver nanoparticles can be synthesized by mixing an aqueous larval gut extract of *Rhynchophorus ferrugineus* with an equal proportion of silver nitrate to provide a solution including *Rhynchophorus ferrugineus* silver nanoparticles. The *Rhynchophorus ferrugineus* silver nanoparticles can be useful as antibacterial agents.

14 Claims, 1 Drawing Sheet

METHOD FOR SYNTHESIZING A SILVER NANOPARTICLE COMPOSITION FROM RHYNCHOPHORUS FERRUGINEUS LARVAE OLIVIER

BACKGROUND

1. Field

The disclosure of the present patent application relates to synthesis of a silver nanoparticle composition, and particularly to synthesis of a silver nanoparticle composition using gut extracts of *Rhynchophorus ferrugineus* Larvae Olivier.

2. Description of the Related Art

Recently, nanoparticles have demonstrated important uses in a variety of fields. Nanoparticles have been used in electronics, sensing, optics, and medicine, for example.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce by-products that pose increased risks to human health and the environment.

In particular, silver and gold nanoparticles may be used as antimicrobial agents against bacteria, viruses, and fungi, including drug-resistant strains of microorganisms. Typically, bacteria have diameters in the micron range, while viruses have diameters less than a micron in size. The fact that the silver nanoparticles are so small allows them to interact readily with such microorganisms. The antimicrobial action occurs because the silver nanoparticles interfere with the enzymatic metabolism of oxygen by the microbes, which effectively "suffocates" and kills the particular microorganism. The nanoscale size of silver nanoparticles means that the particles have a very large surface area, therefore only a small volume of silver nanoparticles is required to act as an effective antagonistic agent.

In recent years, green or environmentally friendly chemical methods have been developed to prepare nanoparticles using plant extracts. Green chemistry has the advantage of being safer, faster, environmentally friendly, and economical. However, the rise of green methods of preparing nanoparticles has also demonstrated that the activities and characteristics of the nanoparticles vary significantly, depending upon the detailed method of synthesis and specific plant extract used. Further, the therapeutic potential of plant extracts has been compromised due to the lack of controlled delivery of an effective dose to the desired target site.

The Red Palm Weevil (RPW), also known as *Rhynchophorus ferrugineus* (Coleoptera: Curculionidae), which can be found in the Mediterranean regions, is regarded as a quarantine pest for tree palms, particularly in urban settings. Prior studies have revealed antibacterial properties of a larval gut extract of *Rhynchophorus ferrugineus* (Red Palm Weevil).

Thus, nanoparticles synthesized using an environmentally friendly method solving the aforementioned problems are desired.

SUMMARY

The present subject matter relates to *Rhynchophorus ferrugineus* silver nanoparticles synthesized from a larval gut extract of *Rhynchophorus ferrugineus* and silver nitrate. The *Rhynchophorus ferrugineus* silver nanoparticles can be useful as antibacterial agents.

In one embodiment, the present subject matter relates to a method of synthesizing *Rhynchophorus ferrugineus* silver nanoparticles, comprising mixing an aqueous larval gut extract from *Rhynchophorus ferrugineus* with silver nitrate to obtain aqueous *Rhynchophorus ferrugineus* silver nanoparticles; and drying the aqueous *Rhynchophorus ferrugineus* silver nanoparticles to obtain the *Rhynchophorus ferrugineus* silver nanoparticles.

In another embodiment, the present subject matter relates to a method of synthesizing *Rhynchophorus ferrugineus* silver nanoparticles, comprising: mixing an aqueous larval gut extract from *Rhynchophorus ferrugineus* with silver nitrate in an equal proportion to obtain aqueous *Rhynchophorus ferrugineus* silver nanoparticles; and drying the aqueous *Rhynchophorus ferrugineus* silver nanoparticles to obtain the *Rhynchophorus ferrugineus* silver nanoparticles having a particle size ranging from about 45 nm to about 90 nm.

In a further embodiment, the present subject matter relates to a pharmaceutical composition, comprising the *Rhynchophorus ferrugineus* silver nanoparticles as produced herein and a pharmaceutically acceptable carrier.

In a still further embodiment, the present subject matter relates to a method of inhibiting bacterial growth in a subject, comprising administering to a subject in need thereof a therapeutically effective amount of the pharmaceutical composition as described herein. Such bacterial growth, for example, can be caused by a multi-drug resistant pathogen.

These and other features of the present subject matter will become readily apparent upon further review of the following specification.

DETAILED DESCRIPTION OF THE PREFERRED EMBODIMENTS

Figure 1:
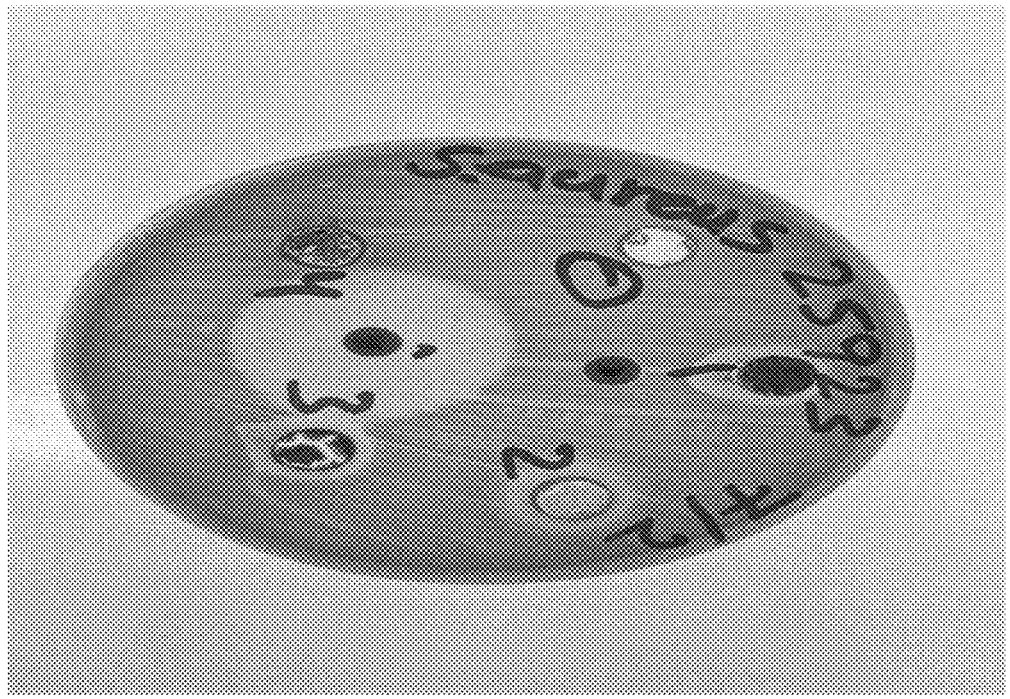
FIG. 1 is an image of the disc used to test sensitivity of *S. aureus* to *Rhynchophorus ferrugineus* silver nanoparticles using a modified Kirby Bauer Disk Diffusion Susceptibility method.

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to *Rhynchophorus ferrugineus* silver nanoparticles (RF-AgNPs) or a "silver nanoparticle composition." The *Rhynchophorus ferrugineus* silver nanoparticles may be synthesized by mixing an aqueous larval gut extract of *Rhynchophorus ferrugineus* with an equal proportion of silver nitrate to provide a solution including *Rhynchophorus ferrugineus* silver nanoparticles or a "silver nanoparticle composition." The solution can be dried and centrifuged to isolate the silver nanoparticle composition. The equal proportion of the aqueous larval gut extract of *Rhynchophorus ferrugineus* and the silver nitrate may be on a weight basis, a volume basis, or a molar basis.

In one embodiment, the aqueous larval gut extract can be prepared by collecting the gut of *Rhynchophorus ferrugineus* larvae and sterilizing the larval gut in any suitable manner, e.g., washing with $H_2O_2$ and water. The extracted larval gut can be soaked in water for a period of time, e.g., about one hour, about two hours, or more, or at least one hour. Then, the extracted larval gut can be milled in water using a grinder to provide a ground mixture. The ground mixture can be centrifuged at, by way of non-limiting example, 10,000 rpm, for about ten minutes, or more, and then incubated for at least about 24 hours, or more, prior to mixing with silver nitrate.

In a further embodiment, the thus-produced aqueous larval gut extract, or supernatant, can be mixed with silver nitrate ($AgNO_3$), for example a 1 mM $AgNO_3$, in an equal proportion. This mixture can be incubated for about 3 hours, 4 hours, 5 hours, or at least 3 hours. The incubation can proceed with shaking during incubation. Following incubation, a color of the mixture may transform from a semi-transparent pale yellow to brown; this color change can start to be observed after about 10-15 minutes of incubation, indicating formation of the AgNPs from the larval gut extracts.

In another embodiment, following completion of the incubation process, the resultant solution can be dried and centrifuged to remove any debris, thus obtaining the *Rhynchophorus ferrugineus* silver nanoparticles. The centrifugation can take place, for example, at about 10,000 rpm, or greater, and for about 10 minutes, or longer. Methanol can optionally be included as a part of the centrifugation process.

In an embodiment, the thus produced *Rhynchophorus ferrugineus* silver nanoparticles can have an average particle size ranging from about 45 nm to about 90 nm, or from about 46 nm to about 87 nm. In other embodiments, the *Rhynchophorus ferrugineus* silver nanoparticles can have an average particle size of about 40 nm, about 45 nm, about 50 nm, about 55 nm, about 60 nm, about 65 nm, about 70 nm, about 75 nm, about 80 nm, about 85 nm, or about 90 nm, or in a range of any two such endpoints.

Another embodiment of the present subject matter is directed to a pharmaceutical composition comprising the *Rhynchophorus ferrugineus* silver nanoparticles and a pharmaceutically acceptable carrier.

A further embodiment of the present subject matter is directed to a method of making a pharmaceutical composition including mixing the *Rhynchophorus ferrugineus* silver nanoparticles with a pharmaceutically acceptable carrier. For example, the method of making a pharmaceutical composition can include mixing the *Rhynchophorus ferrugineus* silver nanoparticles under sterile conditions with a pharmaceutically acceptable carrier with preservatives, buffers, and/or propellants to create the pharmaceutical composition.

To prepare the pharmaceutical composition, the *Rhynchophorus ferrugineus* silver nanoparticles, as the active ingredient, can be intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in an oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by injection, inhalation or insufflation. The *Rhynchophorus ferrugineus* silver nanoparticles can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the *Rhynchophorus ferrugineus* silver nanoparticles or an amount effective to treat a disease, such as a bacterial infection, may be determined initially from the Examples described herein and adjusted for specific targeted diseases using routine methods.

The *Rhynchophorus ferrugineus* silver nanoparticles can have antibacterial properties and can be particularly effective agents against multi-drug resistant pathogenic bacteria. The *Rhynchophorus ferrugineus* silver nanoparticles can thus be safely administered to a subject in need thereof. In an embodiment, the present subject matter relates to a method of inhibiting bacterial growth, treating a bacterial infection, and/or promoting an anti-bacterial response in a subject comprising administering the *Rhynchophorus ferrugineus* silver nanoparticles to a subject in need thereof. Once administered, the *Rhynchophorus ferrugineus* silver nanoparticles can inhibit bacterial growth, treat a bacterial infection, and/or promote an anti-bacterial response in the subject, as well as provide the same activity level against various multi-drug resistant pathogens more broadly.

In an embodiment, the *Rhynchophorus ferrugineus* silver nanoparticles can be administered to a subject to inhibit the growth of *Escherichia coli* (*E. coli*). In an embodiment, the *Rhynchophorus ferrugineus* silver nanoparticles can be administered to a subject to inhibit the growth of *Staphylococcus aureus* (*S. aureus*).

An embodiment of the present subject matter is directed to a method of inhibiting bacterial growth in a subject, comprising administering to a subject in need thereof a therapeutically effective amount of the pharmaceutical composition according to the present subject matter.

The *Rhynchophorus ferrugineus* silver nanoparticles or pharmaceutical compositions thereof can be administered to a subject or a patient by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea. The subject or patient to be treated can be a mammal, for example, including a human.

The present teachings are illustrated by the following examples.

EXAMPLES

Example 1

Synthesis of Silver Nanoparticle Composition

The gut of *Rhynchophorus ferrugineus* larvae ("larval gut extract") was collected from *Rhynchophorus ferrugineus* larvae found in Al-Ahsa Farm, Saudi Arabia. The larval gut extract was surface-sterilized using a 5% $H_2O_2$ wash for 5 minutes, followed by multiple rinses with sterile distilled water. Then, the larval gut extract was soaked in distilled water for 1 hour to remove the remaining materials in the larval gut. The larval gut extract was milled in 10 mL of sterile distilled water, using a grinder for 10 minutes. The ground mixture was centrifuged at 10,000 rpm for 15 minutes, and the supernatant was transferred into a brown bottle and kept in the dark for 24 hours. After incubation, the supernatant was mixed with an equal proportion of freshly prepared silver nitrate (1 mM $AgNO_3$) and incubated for 3 hours with shaking. A transformation of the color of the solution from a semi-transparent pale yellow to brown was observed after 10 to 15 minutes of incubation, which indicated the formation of AgNPs from the larval gut extract, or RF-AgNPs. The Ag particle solution was dried and centrifuged using methanol at 10,000 rpm for 10 min to remove the debris.

Example 2

Sensitivity to Pathogenic Strains

The sensitivity of pathogenic strains to the silver nanoparticle composition was assayed through a modified Kirby Bauer Disk Diffusion Susceptibility method using agar well diffusion. Sterilized paper discs were saturated with 30 µL of the silver nanoparticle composition. Discs were dried and placed on the surface of nutrient agar medium inoculated with bacterial suspensions (*S. aureus* and *E. coli*) prepared in physiological saline. Plates were kept for 2 h at 4° C. to ensure diffusion of the bioactive material, after which the plates were incubated at 37° C. Discs containing 30 µL of sterilized distilled water were left to dry and used as negative controls, whereas positive control sets included discs of the antibiotic chloramphenicol at a concentration of 5%. Plates were incubated for 24 h and diameter of inhibition zones (mm) were measured in triplicates and the average standard deviation was recorded.

FIG. 1 shows the sensitivity of *S. aureus* to different concentrations of the nanoparticle composition (indicated by the numbers "1," "2," and "3"), silver nanoparticles alone (indicated by "4"), and larval gut extracts alone (indicated by "0").

Figure 2:
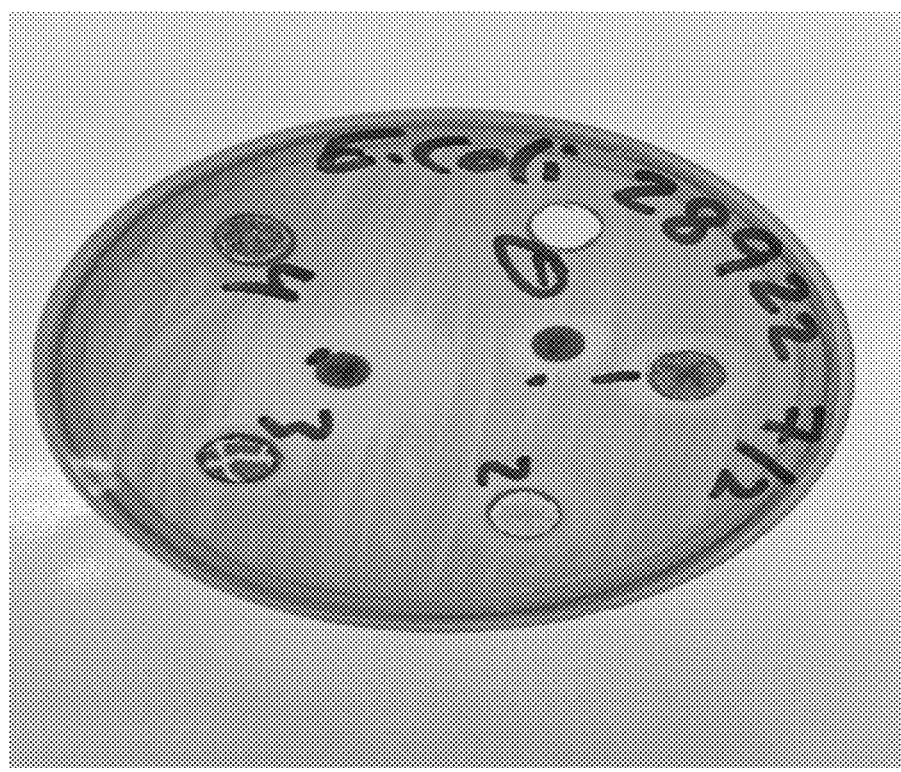
FIG. 2 is an image of the disc used to test sensitivity of *E. coli* to *Rhynchophorus ferrugineus* silver nanoparticles using a modified Kirby Bauer Disk Diffusion Susceptibility method.

FIG. 2 shows the sensitivity of *E. coli* to different concentrations of the nanoparticle composition (indicated by the numbers "1," "2," and "3"), silver nanoparticles alone (indicated by "4"), and larval gut extracts alone (indicated by "0").

It is to be understood that the synthesis of *Rhynchophorus ferrugineus* silver nanoparticles described herein are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing *Rhynchophorus ferrugineus* silver nanoparticles, comprising:
    mixing an aqueous larval gut extract from *Rhynchophorus ferrugineus* comprising a larval gut extract collected from *Rhynchophorus ferrugineus*, sterilized, and milled in water with silver nitrate to obtain aqueous *Rhynchophorus ferrugineus* silver nanoparticles, the aqueous larval gut extract and the silver nitrate being of equal proportions; and
    drying the aqueous *Rhynchophorus ferrugineus* silver nanoparticles to obtain the *Rhynchophorus ferrugineus* silver nanoparticles, wherein the *Rhynchophorus ferrugineus* silver nanoparticles have an average particle size ranging from about 45 nm to about 90 nm.

2. The *Rhynchophorus ferrugineus* silver nanoparticles prepared according to the method of claim 1.

3. A pharmaceutical composition, comprising the *Rhynchophorus ferrugineus* silver nanoparticles of claim 2 and a pharmaceutically acceptable carrier.

4. A method of inhibiting bacterial growth in a subject, comprising administering to a subject in need thereof a therapeutically effective amount of the pharmaceutical composition of claim 3.

5. The method of claim 4, wherein the pharmaceutical composition inhibits the growth of *Escherichia coli*.

6. The method of claim 4, wherein the pharmaceutical composition inhibits the growth of *Staphylococcus aureus*.

7. The method of claim 4, wherein the bacterial growth is caused by a multi-drug resistant pathogen.

8. A method of synthesizing *Rhynchophorus ferrugineus* silver nanoparticles, comprising:
    mixing an aqueous larval gut extract from *Rhynchophorus ferrugineus* comprising a larval gut extract collected from *Rhynchophorus ferrugineus*, sterilized, and milled in water with silver nitrate in an equal proportion to obtain aqueous *Rhynchophorus ferrugineus* silver nanoparticles; and
    drying the aqueous *Rhynchophorus ferrugineus* silver nanoparticles to obtain the *Rhynchophorus ferrugineus* silver nanoparticles having a particle size ranging from about 45 nm to about 90 nm.

9. The *Rhynchophorus ferrugineus* silver nanoparticles prepared according to the method of claim 8.

10. A pharmaceutical composition, comprising the *Rhynchophorus ferrugineus* silver nanoparticles of claim 9 and a pharmaceutically acceptable carrier.

11. A method of inhibiting bacterial growth in a subject, comprising administering to a subject in need thereof a therapeutically effective amount of the pharmaceutical composition of claim 10.

12. The method of claim 11, wherein the pharmaceutical composition inhibits the growth of *Escherichia coli*.

13. The method of claim 11, wherein the pharmaceutical composition inhibits the growth of *Staphylococcus aureus*.

14. The method of claim 11, wherein the bacterial growth is caused by a multi-drug resistant pathogen.

* * * * *